(12) United States Patent
Gilmore et al.

(10) Patent No.: US 10,004,421 B2
(45) Date of Patent: Jun. 26, 2018

(54) DISPOSABLE PROTECTIVE OVERLAY COVERING FOR BIOMEDICAL SENSORS

(71) Applicant: ALTEC, INC., Boston, MA (US)

(72) Inventors: L. Donald Gilmore, Wellesley, MA (US); Carlo J. De Luca, Wellesley, MA (US)

(73) Assignee: Altec, Inc., Boston, MA (US)

( * ) Notice: Subject to any disclaimer, the term of this patent is extended or adjusted under 35 U.S.C. 154(b) by 542 days.

(21) Appl. No.: 14/026,521

(22) Filed: Sep. 13, 2013

(65) Prior Publication Data

US 2015/0080697 A1   Mar. 19, 2015

(51) Int. Cl.
*A61B 5/0492*   (2006.01)
*H05F 3/00*   (2006.01)
*A61B 5/00*   (2006.01)

(52) U.S. Cl.
CPC .......... *A61B 5/0492* (2013.01); *A61B 5/6833* (2013.01); *H05F 3/00* (2013.01); *A61B 2560/0412* (2013.01); *A61B 2562/182* (2013.01)

(58) Field of Classification Search
CPC .................................................. A61B 5/6833
See application file for complete search history.

(56) References Cited

U.S. PATENT DOCUMENTS

| | | | |
|---|---|---|---|
| 5,125,405 A * | 6/1992 | Schmid | A61B 5/04087 600/391 |
| 5,217,013 A * | 6/1993 | Lewis | A61B 5/0091 356/41 |
| 6,047,202 A | 4/2000 | Finneran et al. | |
| 6,238,338 B1 | 5/2001 | DeLuca et al. | |
| 6,440,067 B1 | 8/2002 | DeLuca et al. | |
| 6,480,731 B1 | 11/2002 | DeLuca et al. | |
| 6,572,636 B1 * | 6/2003 | Hagen | A61B 5/02427 600/479 |
| 6,597,944 B1 | 7/2003 | Hadas | |
| 6,687,524 B1 | 2/2004 | Svejk | |
| 6,950,688 B2 | 9/2005 | Axelgaard et al. | |
| 7,627,358 B2 | 12/2009 | Finneran et al. | |

(Continued)

FOREIGN PATENT DOCUMENTS

WO   WO 2006/094513 A2   9/2006
WO   WO 2007/095457         8/2007

(Continued)

OTHER PUBLICATIONS

U.S. Appl. No. 13/747,882, filed Jan. 23, 2013, Gilmore et al.

*Primary Examiner* — Luther G Behringer
(74) *Attorney, Agent, or Firm* — Muirhead and Saturnelli, LLC (57) ABSTRACT

A disposable, low profile sensor overlay covering for use with biomedical sensors and which includes a framework of flexible component layers supporting an arrangement of electrostatic shielding, insulating, cushioning, and electrically conductive adhesive substrate components configured to form a protective covering encasing the sensor. The combination of component layers provides a means to stabilize the relative position of the sensor with respect to the skin and reduce the potential for sensor dislodgment. The mechanical and electrical configurations act in synergy to shield the sensor from external electrical fields and suppress movement artifact.

27 Claims, 9 Drawing Sheets

(56) References Cited

U.S. PATENT DOCUMENTS

| | | |
|---|---|---|
| 7,697,999 B2 | 4/2010 | Axelgaard |
| 7,957,785 B2 | 6/2011 | Nishimura |
| 8,032,210 B2 | 10/2011 | Finneran et al. |
| 8,036,849 B2 | 10/2011 | Kim et al. |
| 8,287,451 B2 | 10/2012 | Ying-Chiang et al. |
| 2005/0096513 A1* | 5/2005 | Ozguz ............... H01L 21/6836 600/301 |
| 2006/0079801 A1 | 4/2006 | DeLuca et al. |
| 2007/0010776 A1* | 1/2007 | Price ................. A61F 13/0203 602/54 |
| 2009/0036792 A1 | 5/2009 | DeLuca et al. |
| 2011/0028823 A1 | 2/2011 | Gilmore et al. |
| 2013/0060098 A1 | 3/2013 | Thomsen et al. |
| 2013/0261422 A1 | 10/2013 | Gilmore et al. |
| 2014/0249397 A1* | 9/2014 | Lake .................. A61B 5/0492 600/386 |
| 2015/0133763 A1* | 5/2015 | Saroka .................... A61B 5/05 600/407 |

FOREIGN PATENT DOCUMENTS

| | | |
|---|---|---|
| WO | WO 2010/100649 A1 | 9/2010 |
| WO | WO 2013/164827 A2 | 11/2013 |

\* cited by examiner

DISPOSABLE PROTECTIVE OVERLAY COVERING FOR BIOMEDICAL SENSORS

FIELD OF INVENTION

The system described herein relates to the field of sensing bio-potentials generated within a living body and more particularly, relates to the securement of sensors placed on the surface of the skin for detecting the electrical activity from muscles using the surface Electromyographic (sEMG) signal.

BACKGROUND

A contracting muscle generates an electrical field that can be sensed with electrodes placed on the skins surface. The resulting voltage is defined as a surface electromyographic (sEMG) signal. Applications for using sEMG signal measurement are diverse and can range from sports and ergonomic activities to clinical evaluation of patients, as well as neuromuscular research applications which investigate motor control. Analysis of the sEMG signal can provide valuable information about muscle performance not obtainable by other means. The sEMG signal amplitude may be representative of force generated by the muscle, which unlike externally applied force measuring devices, can be used to assess the individual force contributions from a group of muscles acting together on a joint. Multiple sEMG sensors placed on the limbs can monitor muscle activity levels and coordination during gait studies, or in neurological disorders such as Parkinson's disease. Changes in a frequency spectra of the sEMG signal resulting from localized muscle fatigue can be used to more objectively assess appropriate activity levels and durations of tasks in the workplace. Using sEMG signal detection and analysis may be a valuable asset when investigating human muscular performance in these types of applications.

Conventionally, the configuration of a sensor designed to detect sEMG signals includes two electrode contacts placed on the skin over the muscle and oriented in a direction parallel to the muscle fibers. A third "reference" contact may be located at an electrically inactive location on the body. Disposable sEMG sensors designed for clinical use may include two electrodes filled with skin impedance reducing electrolytic gel or formed from hydrophilic gel; one for each signal input placed singularly, or in pairs, mounted on a flexible non-conductive pad adhered to the skin over the muscle. In some sensors, the two signal and reference contacts are placed on the same insulating pad in the form of an equilateral triangle. The electrodes are attached by snaps or spring loaded clips and connected to remote electronic preamplifier circuitry via individual lead wires. The preferred recording configuration is the single differential configuration where the voltage at each signal input contact is measured with respect the third reference contact and subtracted using a differential pre-amplifier circuit.

In addition, encased sEMG sensor designs incorporating integrated preamplifier circuitry with signal and reference electrode contacts secured to the bottom eliminate the need for individual lead wires and associated snaps or spring loaded clips. The sEMG signal output of these designs may be tethered to data acquisition hardware using a thin cable or can be completely wireless.

Despite recent advancements in sensor designs, sensors may still retain limited functionality in demanding applications, such as when recording data in uncontrolled movement disorders, in many sports activities, or in the work place environment. The widespread utilization of sEMG technology outside the laboratory environment has been limited by several factors related to the nature of the sEMG signal: The voltage amplitude of sEMG component of the signal detected by a sensor is inherently small, ranging from 10 microvolts to several millivolts. In addition to the sEMG signal component, the voltage at the sensor output includes the contribution from other noise sources generated by the inherent noise of the sensor's electronics, the electrolytic interface established between the metallic contacts of the sensor and intervening tissue, and artifact voltages induced from the movement of the sensor contacts with respect to the intervening tissue. Externally induced voltages from power lines and electrostatic (triboelectric) sources can also contaminate the detected sEMG signal. The magnitude of the contaminating electrostatic and movement artifact noise sources can be equal to or exceed the magnitude of the sEMG component of the sensors signal output when used in vigorous clinical, sports, and ergonomic activities, such as when monitoring neurologically impaired patients with flailing limbs, athletes performing jumping and throwing movements, or workers exposed to sudden accelerations and impacts. The problems of movement artifact and sensitivity to electro-static fields are especially severe when the sensor is placed under clothing garments. Even normal activities such as walking can induce electro-static voltage artifacts as a result of walking on carpet or contact with certain fabrics under low humidity conditions. These artifacts could easily be misinterpreted as muscle activity. Current sensor technologies restrict the user to conventional laboratory assessments; e.g. during sustained or repeated isometric contractions or during non-demanding dynamic tasks that are encountered in daily life, such as reaching for an object, walking/climbing stairs, lifting an object, or doing other non-vigorous, low-velocity activities. There may be additional burden to the subject and researcher on occasions when the subject is asked to change into a t-shirt and/or shorts prior to being instrumented so that no obstructions to the sensor from clothing are encountered.

All of the aforementioned tethered and wireless sensor configurations offer only a limited set of solutions for detecting high fidelity sEMG signals in applications involving dynamic contractions. The susceptibility of the described sensors to induced movement artifacts precludes use in vigorous applications and during conditions where electro-static fields may be generated such as sensor placement under an individual's clothing. The common practice of using adhesive tapes and bandages to secure the sensor to the skin can exacerbate the generation of electrostatic charge when in contact with garments.

It would be an improvement to provide a disposable sensor overlay covering configuration that secures and shields the sensor from mechanical and electrostatic disturbances when used under clothing.

SUMMARY OF THE INVENTION

The system described herein includes a disposable, low profile sensor overlay covering for use with biomedical sensors including a framework of flexible component layers supporting an arrangement of electrically shielding, insulating, cushioning, and electrically conductive adhesive substrate components configured to form a protective covering encasing the sensor. The combination of component layers provides a means to stabilize the relative position of the sensor with respect to the skin and reduce the potential for sensor dislodgment. The mechanical and electrical configurations act in synergy to shield the sensor from external electrical fields and suppress movement artifact.

The system described herein relates to an improved type of biomedical sensor overlay covering that secures and shields the sensor from mechanical and external electrical interference disturbances when used under clothing. Unlike existing sensor coverings using double sided tapes or tape strips applied over the sensor, the system described herein incorporates features that can mold to the contours of the underlying musculature and flex with skin movement and cushion the sensor from the effects of direct mechanical contact disturbances. Furthermore, the integral shielding membrane is designed to dissipate the accumulation of electrostatic charges to the skin, and to allow for the transmission and reception of radio frequency signals from encased wireless biomedical sensors.

According to one feature of the system described herein, the biomedical sensor overlay covering is configured as a framework of flexible component layers supporting an arrangement of electrically conductive shielding, electrically insulating, cushioning, and electrically conductive adhesive substrate component layers, configured to form a flexible protective contoured covering that envelops and mechanically stabilizes the sensor, securing it to the skin.

According to another feature of the system described herein, the biomedical sensor overlay covering is in the form of a flexible, elongated strip, with a receptacle region shaped and contoured to retain a biomedical sEMG sensor and conductive adhesive regions securing the sensor to the skin, thereby dissipating electrostatic charges to the body through contact with the skin's surface.

According to another feature of the system described herein, the biomedical sensor overlay covering is in the alternative form of a continuous band, with a receptacle region shaped and contoured to retain a biomedical sEMG sensor and encircle a limb with conductive adhesive regions securing the sensor to the skin, thereby dissipating electrostatic charges to the body through contact with the skin's surface.

According to another feature of the system described herein, the biomedical sensor overlay covering contains segments of stretchable elastic providing compliance with the underlying skin tissue.

According to another feature of the system described herein, the biomedical sensor overlay covering is in the alternative form of a patch, with a receptacle region shaped and contoured to retain a biomedical sEMG sensor, and perimeter electrically conductive adhesive regions securing the sensor to the skin, thereby dissipating electrostatic charges to the body through contact with the skin's surface.

According to another feature of the system described herein, the biomedical sensor overlay covering can be used with tethered and wireless sensor technologies.

According to yet another feature of the system described herein, the biomedical sensor overlay covering contains an electro-static shield substrate layer formed from an electrically conductive material.

According to another feature of the system described herein, the electrostatic shield substrate layer is alternatively formed from electrically resistive material.

According to another feature of the system described herein, the conductive and resistive materials of the electrostatic shield substrate layers are formed with a plurality of apertures.

According to another feature of the system described herein, the electrostatic shield substrate layer is alternatively formed from electrically non-conductive material with a plurality of electrically conductive traces.

According to another feature of the system described herein, the electrically conductive traces of the non-conductive electrostatic shield substrate layer are in the form of a printed circuit.

According to another feature of the system described herein, the electrical conductivity, and geometrical configuration of the apertures and traces of the electrostatic shield substrate layer provide a means of ingress and egress for radio frequency signal reception and transmission.

According to another feature of the system described herein, the biomedical sensor overlay covering contains a body-directed electrostatic shield contact pad substrate layer formed from electrically conductive, adhesive, cross-linked hydrophilic polymer gel establishing a mechanical and electrical contact between the electrostatic shield substrate layer and the surface of the skin, thereby dissipating electrostatic charges to the body.

According to another feature of the system described herein, an electrically insulating substrate layer, contoured to match the profile of the electrostatic shield substrate layer, forms an insulating barrier between the electrostatic shield and the sensor.

According to another feature of the system described herein, the insulating substrate layer is shaped so as to selectively expose, electrically conductive regions of the electrostatic shield substrate layer to the electrostatic shield contact pad substrate layer.

According to yet another feature of the system described herein, a cushioning substrate layer, contoured and shaped to match the upper surfaces of the sensor is adhered to the lower surface of the insulating substrate layer so that it makes mechanical contact.

According to another feature of the system described herein, the cushioning substrate layer is formed from absorbent open cell foam or interwoven fibers arranged so that they wick away and retain excessive skin moisture.

According to another feature of the system described herein the component materials are hypoallergenic, breathable, and designed for use without slippage or skin breakdown.

According to another feature of the system described herein, the sensor overlay covering is cosmetically textured and colored so that it more closely matches the color and texture of the underlying skin.

According to another feature of the system described herein, the body-directed adhesive surfaces of the sensor overlay covering are mounted on a release liner.

According to another feature of the system described herein, the sensor overlay covering is single use and disposable. The sensor overlay cushions the sensor suppressing movement artifacts, molds to the contours of the skin, and flexes with skin movement. An integral electrically conducting shield mitigates the effects of electro-static and externally generated electrical fields. The disposable sensor overlay may be used in conjunction with both existing tethered and wireless sensor technologies. The combination of these features represents innovations not found in comparable sensor systems and significantly expands the ability of researchers and clinicians to investigate human movement and muscle function during clinical, sports, and ergonomic applications.

DESCRIPTION OF THE DRAWINGS

These and other objects and features of the system described herein will become more apparent upon perusal of the following description taken in conjunction with the accompanying drawings wherein:

FIG. 1b is a top and a cross-sectional view of the sensor overlay covering shown in FIG. 1a;

FIG. 3b is a top and a cross-sectional view of the sensor overlay covering shown in FIG. 3a;

FIG. 7b is a top and a cross-sectional view of the sensor overlay covering shown in FIG. 7a;

FIG. 9a is a side pictorial view of the sensor overlay covering shown in FIG. 7 secured to the leg;

FIG. 9b is a close up view of the sensor overlay covering shown in FIG. 9a;

DESCRIPTION OF VARIOUS EMBODIMENTS

Figure 1A:
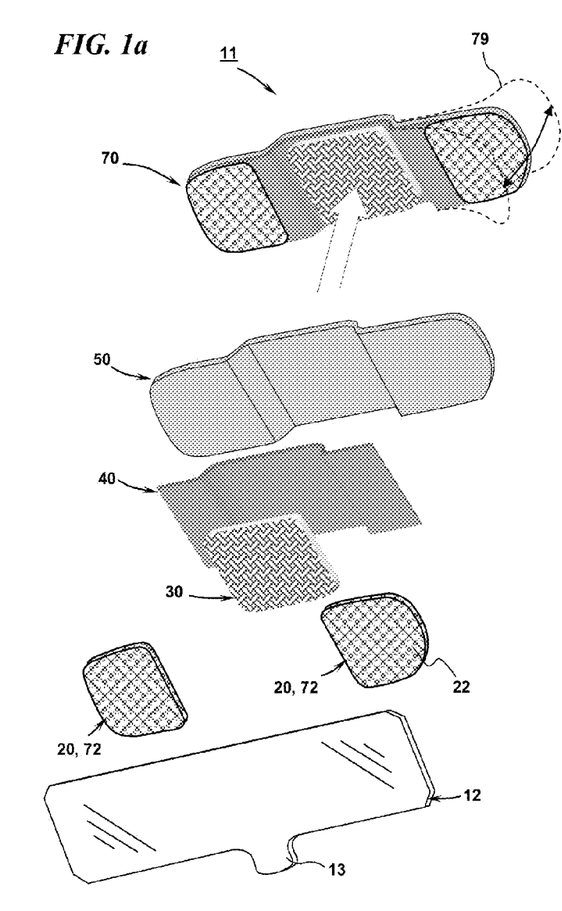
FIG. 1a is an exploded view of a biomedical sensor overlay covering according to the system described herein.

A biomedical sensor overlay covering 11 includes an electrostatic shield contact pad substrate layer 20, a cushioning substrate layer 30, an insulating substrate layer 40, and an electrostatic shield substrate layer 50, disposed on a release liner 12 as illustrated in the exploded view of FIG. 1a. The assembled components of the sensor overlay covering 11 are in the form of a flexible, elongated strip 70, with a receptacle region shaped and contoured to retain a biomedical sEMG sensor and conductive adhesive regions 20 securing the sensor to the skin. The assembled components of the sensor overlay covering 11 are configured so as to dissipate the accumulation of electrostatic charges on the covering's outer surface 78 into the body and shield the underlying sensor from externally generated low frequency electrical fields such as power line interference. The open-sided geometry of the sensor overlay covering 11 provides compatibility with passive sensor configurations comprised of surface electrode contacts terminated with lead wires, or tethered sensor configurations with active electronics terminated by cable. The constructional architecture of the sensor overlay covering 11 is detailed in FIG. 1b which shows a top view 80, cross-sectional views 25, 35, 45, 55 of each subsequently added substrate layer, and a cross-sectional view 75 of the assembled components, each of which are individually described.

Figure 1B:
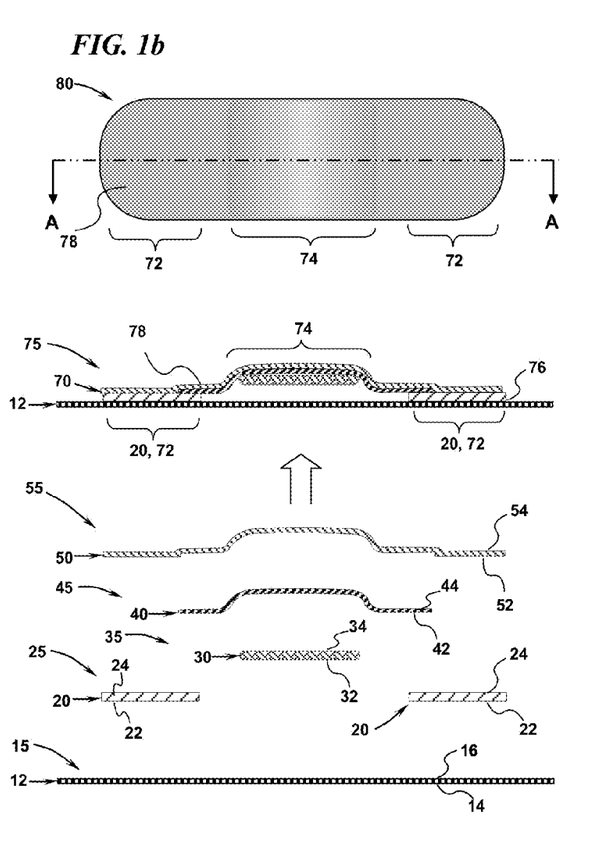

The electrostatic shield contact pad substrate layer 20 of the sensor overlay covering 11 includes two, electrically conductive, adhesive, cross-linked hydrophilic polymer gel sheets whose top surface 24 is disposed on regions 72 of the bottom surface 52 of the electrostatic shield substrate layer 50 establishing a mechanical and electrical contact with the electrostatic shield substrate layer 50. Each electrostatic shield contact pad substrate layer 20 is shaped and contoured to match the profile of the regions 72 of the electrostatic shield substrate layer 50. The body-directed surface 22 of the electrostatic shield contact pad substrate layer 20 establishes a mechanical and electrical contact between the electrostatic shield substrate layer 50 and the surface of the skin, thereby dissipating electrostatic charges to the body and securing the sensor overlay covering 11.

The cushioning substrate layer 30 of the sensor overlay covering 11 includes a flexible, compliant, mat whose upper surface 34 is disposed on and adhered to the lower surface 42 of the insulating substrate layer 40 so that it makes mechanical contact in retaining region 74. The thickness, compliance and contour of the cushioning substrate layer 30 is selected so that when the sensor overlay covering 11 is applied over a sensor, its lower surface 32 conforms to the upper surfaces of a sensor, thereby retaining and cushioning the sensor from externally applied mechanical disturbances. The cushioning substrate layer 30 component of the sensor overlay covering 11 is formed from a sheet of non-triboelectric, absorbent material with permeability and thickness selected so that it wicks away and retains excessive skin moisture.

The insulating substrate layer 40 of the sensor overlay covering 11 includes a flexible, compliant sheet of electrically insulating material whose upper surface 44 is disposed on and adhered to the lower surface 52 of the electrostatic shield substrate layer 50 so that it makes mechanical contact and forms an electrically insulating barrier between the electrostatic shield 50 and a sensor. The profile of insulating substrate layer 40 is shaped so as to selectively expose, electrically conductive regions 72 of the bottom surface 52 of the electrostatic shield substrate layer 50 to the upper surface 24 of the electrostatic shield contact pad substrate layer 20, so as to form an electrical inter-connection between the electrostatic shield layer 50 and contact pad substrate layer 20. The insulating substrate layer 40 is formed from a double-sided adhesive coated sheet of non-triboelectric, material with thickness selected so that the material resists electrical breakdown from static electrical discharges (ESD) to the skin.

The electrostatic shield substrate layer 50 of the sensor overlay covering 11 includes a flexible, compliant layer with electrically conductive properties configured so as to dissipate the accumulation of electrostatic charges on the covering's outer surface 78 into the body, and shield the underlying sensor from externally generated electrical fields. The contoured region 74 of the electrostatic shield substrate layer 50 is shaped to retain a biomedical sensor. The upper surface 54 of the electrostatic shield substrate layer 50 forms the outer covering 78 of the sensor overlay 11 which is cosmetically textured and colored so that it more closely matches the color and texture of the underlying skin. The exposed regions 72 of the body directed surface 52 of the electrostatic shield substrate layer 50 form a mechanical and electrical inter-connection with the upper surfaces 24 of the electrostatic shield contact pad substrate layer 20.

Figures 2A, 2B, 2C, 2D:
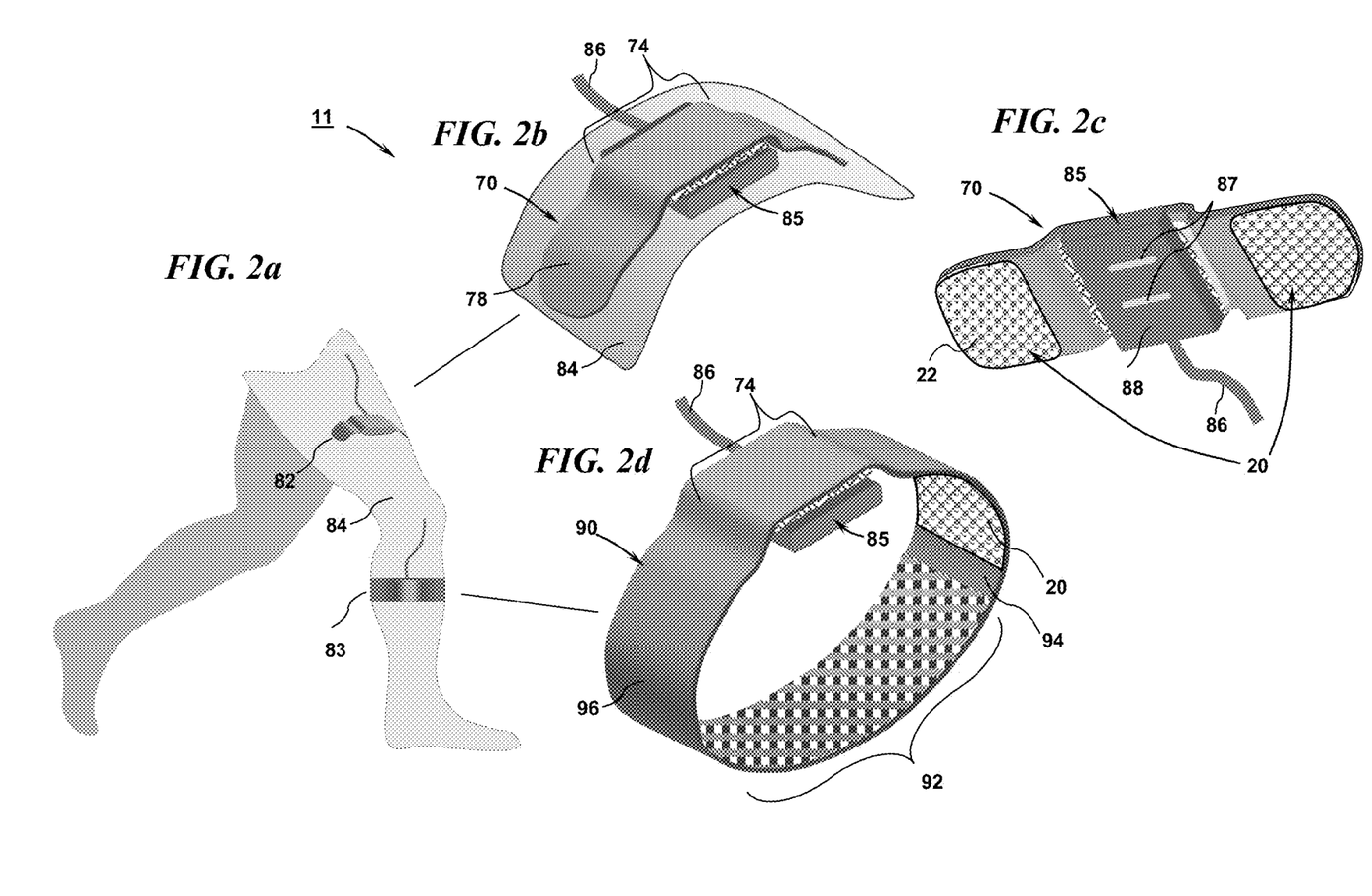
FIG. 2a is a side pictorial view of the sensor overlay covering shown in FIG. 1 secured to the leg.
FIG. 2b is a close up view of the sensor overlay covering shown in FIG. 2a shown secured to the upper leg.
FIG. 2c is a bottom view of the sensor overlay covering shown in FIG. 2b showing the body-directed substrate layers.
FIG. 2d is a close up view of an alternative sensor overlay covering shown in FIG. 2a with a continuous band encircling the lower leg.

Pictorial views of the assembled components of the elongated strip configuration 70 of the sensor overlay covering embodiment 11 and an alternative configuration where the elongated strip 70 is formed into a continuous band 90 are shown in FIGS. 2a, 2b, 2c, and 2d. As illustrated in the example use-cases in FIG. 2a, the elongated strip configuration 70 is placed on the muscles of the upper leg 82. FIG. 2b details a close up view of the elongated strip configuration 70 positioned on the skin 84. A tethered sensor 85 is retained in a receptacle region 74 of overlay configuration 70 so that the sensor's cable 86 is unencumbered. FIG. 2c shows a bottom view of the sensor retained in the overlay configuration 70 and arranged so that the sensor's bottom surface 88 containing the sensor contacts 87 and the surfaces 22 of the electrostatic shield contact pad substrate layer 20 are directed towards the skin. The elongated strip configuration 70 of the sensor overlay covering embodiment 11 is suitable for securing the sensor at locations which are not amenable to an encircling band, such as the torso and large limb muscles, or in locations where an encircling band would encumber movement such as sensor placements on the hand, neck and face. As further illustrated in example use-case in FIG. 2a, an alternative continuous band overlay configuration 90 may be suitable for a secure sensor placement on smaller limb muscles such as the lower leg 83, especially for applications monitoring sEMG activity during vigorous, dynamic limb movements such as walking and running FIG. 2d shows a close up view of the continuous band overlay configuration 90. The geometrical configuration and structural architecture is similar to the elongated strip configuration 70, including a receptacle region 74 shaped and contoured to retain a biomedical sEMG sensor 85, with the addition of segments of stretchable elastic 92 which form the overlay covering into a continuous band 90 for encircling the limb, while providing compliance with the underlying skin tissue.

The skin 84 application of the configurations 70, 90 of sensor overlay covering 11 used the examples illustrated in FIG. 2a, is detailed as follows: Initially, the body-directed surface 88 of the sensor 85 containing the electrode contacts 87 is applied to the surface of the skin 84. Prior to use, the release liner 12 of overlay configuration 70 is removed and the retaining region 74 of overlay covering 70 is positioned and pressed into place over the sensor 85. Next, the exposed body-directed surfaces 22 of each of the electrostatic shield contact pads 20 are applied to the surface of the skin 84, and the outer surface 78 of the overlay 70 is pressed to the skin 84, securing the sensor 85 and overlay covering configuration 70. Application of the continuous band overlay configuration 90 follows a similar procedure as described for the application of the elongated strip overlay configuration 70 with the exception that the release liner 12 covering the body-directed surfaces 22 of each of the electrostatic shield contact pads 20 is not removed prior to the application of the sensor overlay band. The sensor 85 is applied to the surface of the skin 84 at position 83 and the elasticized region 92 of band overlay configuration 90 is stretched so that the band can be placed into position 83 over the limb so that the retaining region 74 of overlay covering configuration 90 is positioned over the sensor 85 as show in the close up view of FIG. 2d. After the retaining region 74 of overlay covering configuration 90 is positioned over the sensor 85, the release liner 12 is removed from the inner surface 94 by pulling on the tab 13, exposing the body-directed surfaces 22 of each of the electrostatic shield contact pads 20. Next, the outer surface 96 of the overlay covering configuration 90 is pressed to the surface of the skin 84, securing the sensor 85 and overlay covering configuration 90.

Figure 3A:
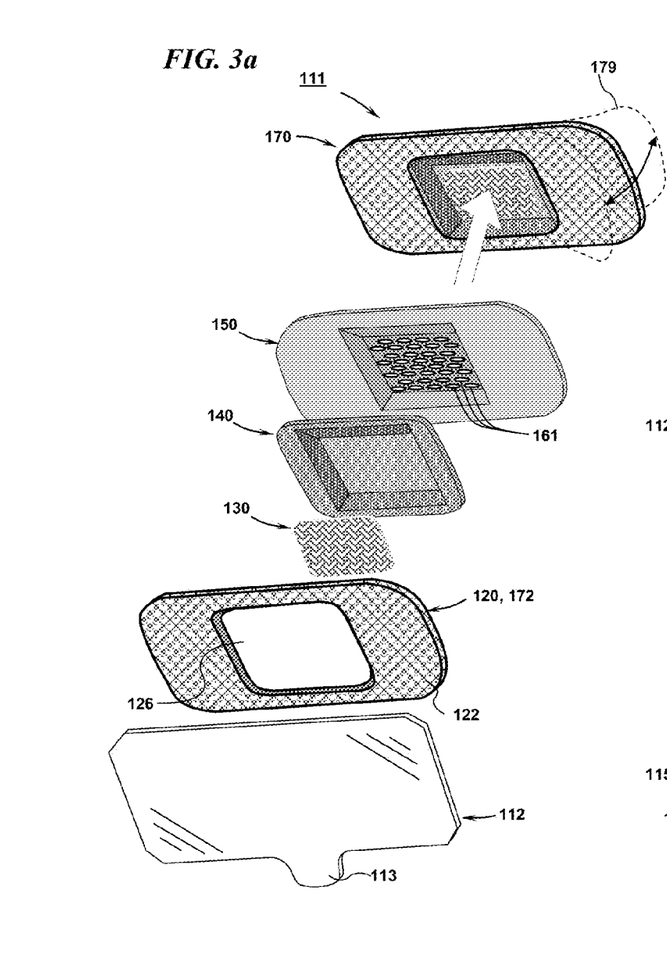
FIG. 3a is an exploded view of another embodiment of the biomedical sensor overlay covering according to the system described herein.

Another biomedical sensor embodiment 111 includes an electrostatic shield contact pad substrate layer 120, a cushioning substrate layer 130, an insulating substrate layer 140, and an electrostatic shield substrate layer 150, disposed on a release liner 112 as illustrated in the exploded view of FIG. 3a. The assembled components of the sensor overlay covering 111 are in the form of a flexible, elongated strip 170, with a receptacle region shaped and contoured to retain a wireless biomedical sEMG sensor and conductive adhesive regions securing the sensor to the skin. The enclosed geometry of the sensor retaining region 174 of the sensor overlay covering 111 is in the form of a contoured pocket 177 designed to be compatible with wireless sensor technologies, and provide a means to dissipate the accumulation of electrostatic charges on the covering's outer surface 178 into the body, and shield the underlying sensor from externally generated low frequency electrical fields such as power line interference while maintaining a means of ingress and egress for radio frequency signal reception and transmission for the wireless sensor. The constructional architecture of the sensor overlay covering 111 is detailed in FIG. 3b which shows a top view 180, cross-sectional views 125, 135, 145, 155 of each subsequently added substrate layer, and a cross-sectional view 175 of the assembled components, each of which are individually described.

Figure 3B:
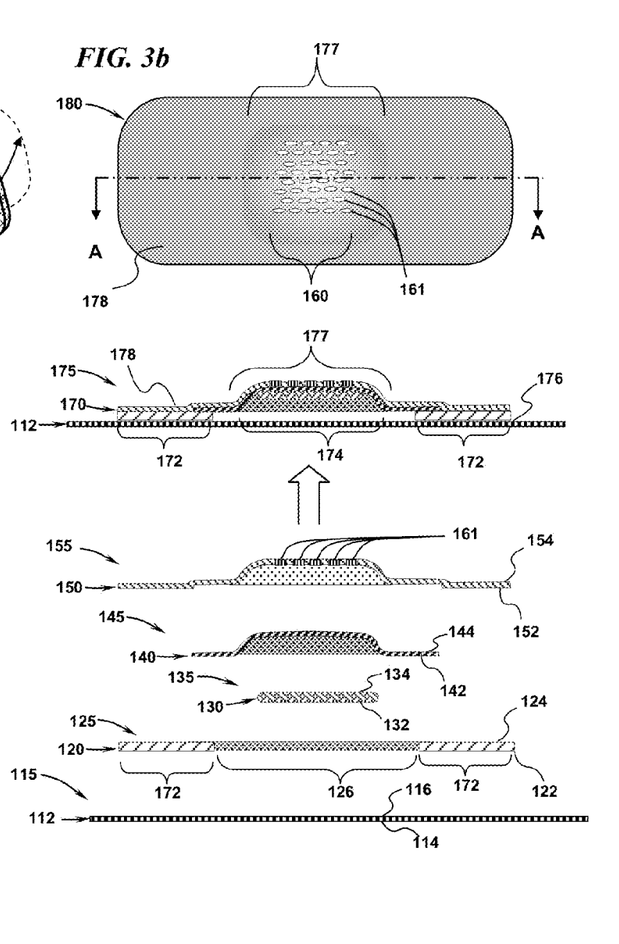

The electrostatic shield contact pad substrate layer 120 of the sensor overlay covering 111 includes an electrically conductive, adhesive, cross-linked hydrophilic polymer gel sheet with an central opening 126, and whose top surface 124 is disposed on region 172 of the bottom surface 152 of the electrostatic shield substrate layer 150 establishing a mechanical and electrical contact with the electrostatic shield substrate layer 150. The electrostatic shield contact pad substrate layer 120 is shaped and contoured to match the profile of the region 172 of the electrostatic shield substrate layer 150. The body-directed surface 122 of the electrostatic shield contact pad substrate layer 120 establishes a mechanical and electrical contact between the electrostatic shield substrate layer 150 and the surface of the skin, thereby dissipating electrostatic charges to the body and securing the sensor overlay covering 111.

The cushioning substrate layer 130 of the sensor overlay covering 111 includes a flexible, compliant, mat whose upper surface 134 is disposed on and adhered to the lower surface 142 of the insulating substrate layer 140 so that it makes mechanical contact in retaining region 174. The thickness, compliance and contour of the cushioning substrate layer 130 is selected so that when the sensor overlay covering 111 is applied over a sensor, its lower surface 132 conforms to the upper surfaces of a sensor, thereby retaining and cushioning the sensor from externally applied mechanical disturbances. The cushioning substrate layer 130 component of the sensor overlay covering 111 is formed from a sheet of non-triboelectric, absorbent material with permeability and thickness selected so that it wicks away and retains excessive skin moisture.

The insulating substrate layer 140 of the sensor overlay covering 111 includes a flexible, compliant sheet of electrically insulating material whose upper surface 144 is disposed on and adhered to the lower surface 152 of the electrostatic shield substrate layer 150 so that it makes mechanical contact and forms an electrically insulating barrier between the electrostatic shield 150 and a sensor. The profile of insulating substrate layer 140 is shaped so as to selectively expose, the electrically conductive region 172 of the bottom surface 152 of the electrostatic shield substrate layer 150 to the upper surface 124 of the electrostatic shield contact pad substrate layer 120, so as to form an electrical inter-connection between the electrostatic shield layer 150 and contact pad substrate layer 120. The insulating substrate layer 140 is formed from a double-sided adhesive coated sheet of non-triboelectric, material with a thickness selected so that it resists electrical breakdown from static electrical discharges (ESD) to the skin.

Figure 4A:
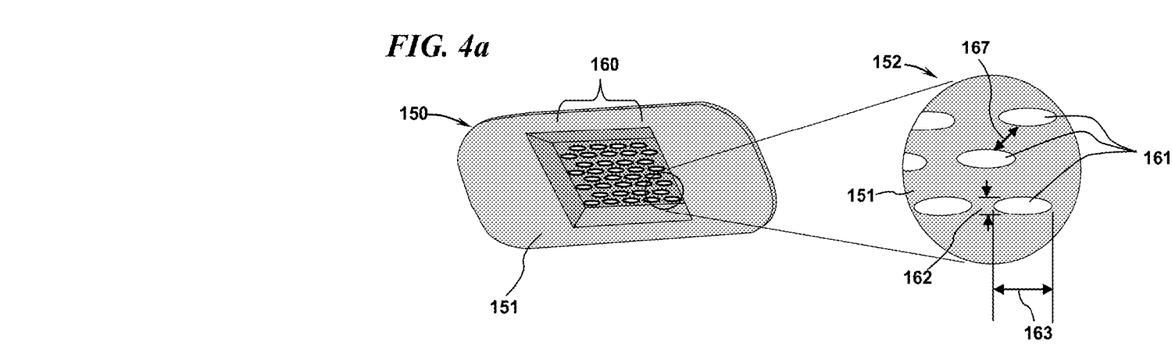
FIG. 4a is an expanded detail view of the electrostatic shield substrate layer of the sensor overlay covering shown in FIG. 3a, showing a conductive substrate with an arrangement of apertures.
Figure 4B:
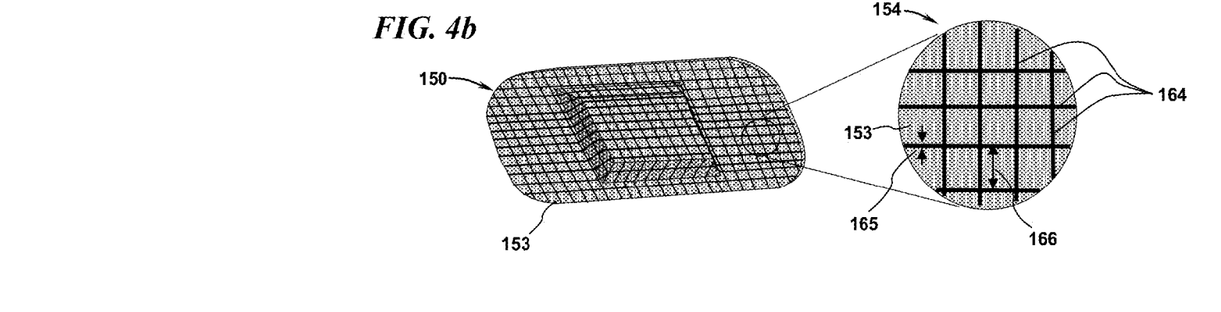
FIG. 4b is an expanded detail view of the electrostatic shield substrate layer of the sensor overlay covering shown in FIG. 3a, showing an non-conductive substrate with an arrangement of conductive traces.
Figure 4C:
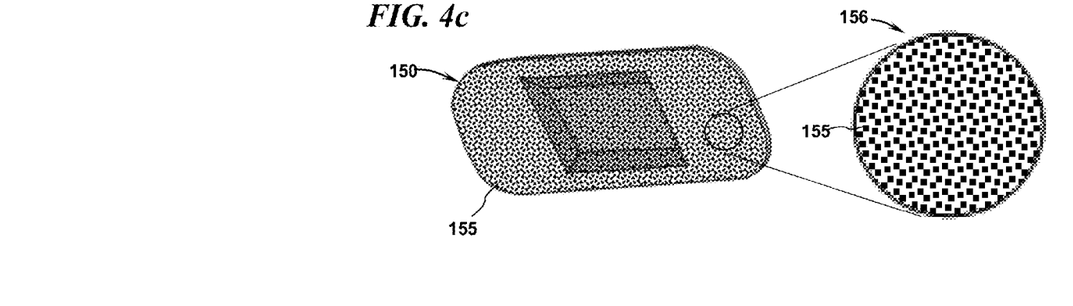
FIG. 4c is an expanded detail view of the electrostatic shield substrate layer of the sensor overlay covering shown in FIG. 3a, showing an electrically resistive substrate.

The electrostatic shield substrate layer 150 of the sensor overlay covering 111 includes a flexible, compliant layer with electrically conductive properties configured so as to dissipate the accumulation of electrostatic charges on the covering's outer surface 178 into the body and shield the underlying sensor from externally generated low frequency electrical fields such as power line interference, while maintaining a means of ingress and egress for radio frequency signal reception and transmission for the wireless sensor. The contoured region 174 of the electrostatic shield substrate layer 150 is shaped to retain and encase a biomedical sensor. The upper surface 154 of the electrostatic shield substrate layer 150 forms the outer covering 178 of the sensor overlay 111 which is cosmetically textured and colored so that it more closely matches the color and texture of the underlying skin. The exposed region 172 of the body directed surface 152 of the electrostatic shield substrate layer 150 forms a mechanical and electrical inter-connection with the upper surface 124 of the electrostatic shield contact pad substrate layer 120. The contoured pocket region 177 of electrostatic shield substrate layer 150 contains an aperture region 160 formed from a plurality of apertures 161. FIG. 4a is pictorial view of an electrically conductive 151 electrostatic shield substrate layer 150, accompanied by an encircled magnified view 152 showing the plurality of apertures 161 forming the aperture region 160. The height 162, width 163, separation 167, and number of apertures within the aperture region 160 of the electrically conductive 151 electrostatic shield substrate layer 150 are selected to maximize the level of ingress and egress of radio frequency signal reception and transmission for a given radio frequency bandwidth of a wireless sensor while maintaining dissipation of electrostatic fields. FIGS. 4b and 4c show two alternative constructional configurations of the of electrostatic shield substrate layer 150. FIG. 4b is pictorial view of an electrically non-conductive 153 electrostatic shield substrate layer 150, accompanied by an encircled magnified view 154 showing a plurality of electrically conductive traces 164 retained in a non-conductive substrate 153. The pattern of traces 164 can be formed using printed circuit board technology, can be formed from a plurality of electrically conductive wires embedded within the electrically non-conductive substrate 153, or formed using other selective electrically conductive trace 164 deposition techniques.

The width 165, spacing 166, and number electrically conductive traces 164 are selected to maximize the level of ingress and egress of radio frequency signal reception and transmission for a given radio frequency bandwidth of a wireless sensor while maintaining dissipation of electrostatic fields. FIG. 4c is pictorial view of an electrically resistive 155 electrostatic shield substrate layer 150, accompanied by an encircled magnified view 156 showing the distribution of resistive composition throughout the electrostatic shield substrate layer 150. The bulk resistivity of the substrate 155 is selected to maximize the level of ingress and egress of radio frequency signal reception and transmission for a given radio frequency bandwidth of a wireless sensor while maintaining dissipation of electrostatic fields.

Figures 5A, 5B, 5C, 5D:
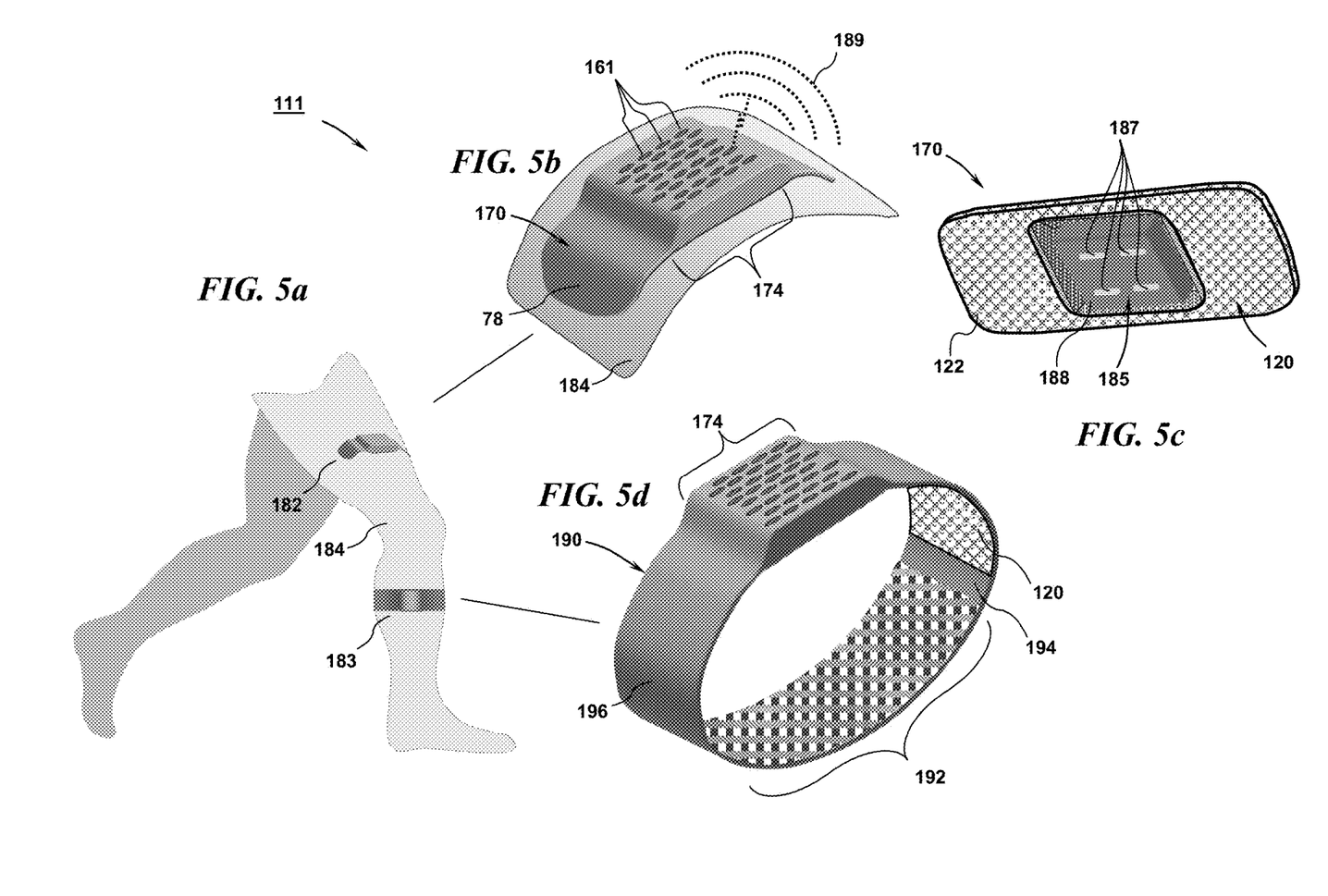
FIG. 5a is a side pictorial view of the sensor overlay covering shown in FIG. 3 secured to the leg.
FIG. 5b is a close up view of the sensor overlay covering shown in FIG. 5a, shown secured to the upper leg.
FIG. 5c is a bottom view of the sensor overlay covering shown in FIG. 5b showing the body-directed substrate layers.
FIG. 5d is a close up view of an alternative sensor overlay covering shown in FIG. 5a with a continuous band encircling the lower leg.

Pictorial views of the assembled components of the elongated strip configuration 170 of the sensor overlay covering embodiment 111 and an alternative configuration where the elongated strip 170 is formed into a continuous band 190 are shown in FIGS. 5a, 5b, 5c, and 5d. As illustrated in the example use-cases in FIG. 5a, the elongated strip configuration 170 is placed on the muscles of the upper leg 182. FIG. 5b details a close up view of the elongated strip configuration 170 positioned on the skin 184. A wireless sensor 185 is retained in a receptacle region 174 of overlay configuration 170. The arrangement of apertures 161 in the sensor overlay covering embodiment 111 proves for the ingress and egress for a radio frequency signal 189. The FIG. 5c shows a bottom view of the sensor retained in the overlay configuration 170 and arranged so that the sensor's bottom surface 188 containing the sensor contacts 187 and the surfaces 122 of the electrostatic shield contact pad substrate layer 120 are directed towards the skin. The elongated strip configuration 170 of the sensor overlay covering embodiment 111 is suitable for securing the sensor at locations which are not amenable to an encircling band, such as the torso and large limb muscles, or in locations where an encircling band would encumber movement such as sensor placements on the hand, neck and face. As further illustrated in example use-case in FIG. 5a, an alternative continuous band overlay configuration 190 may be suitable for a secure sensor placement on smaller limb muscles such as the lower leg 183, especially for applications monitoring sEMG activity during vigorous, dynamic limb movements such as walking and running FIG. 5d shows a close up view of the continuous band overlay configuration 190. The geometrical configuration and structural architecture is similar to the elongated strip configuration 170, including a receptacle region 174 shaped and contoured to retain a biomedical sEMG sensor 185, with the addition of segments of stretchable elastic 192 which form the overlay covering into a continuous band 190 for encircling the limb, while providing compliance with the underlying skin tissue.

The skin 184 application of the configurations 170, 190 of sensor overlay covering 111 used the examples illustrated in FIG. 5a, is detailed as follows: Initially, the body-directed surface 188 of the sensor 185 containing the electrode contacts 187 is applied to the surface of the skin 184. Prior to use, the release liner 112 of overlay configuration 170 is removed and the retaining region 174 of overlay covering 170 is positioned and pressed into place over the sensor 185. Next, the exposed body-directed surfaces 122 of the electrostatic shield contact pad 120 is applied to the surface of the skin 184, and the outer surface 178 of the overlay 170 is pressed to the skin 184, securing the sensor 185 and overlay covering configuration 170. Application of the continuous band overlay configuration 190 follows a similar procedure as described for the application of the elongated strip overlay configuration 170 with the exception that the release liner 112 covering the body-directed surfaces 122 of the electrostatic shield contact pad 120 is not removed prior to the application of the sensor overlay band. The sensor 185 is applied to the surface of the skin 184 at position 183 and the elasticized region 192 of band overlay configuration 190 is stretched so that the band can be placed into position 183 over the limb so that the retaining region 174 of overlay covering configuration 190 is positioned over the sensor 185 as show in the close up view of FIG. 5d. After the retaining region 174 of overlay covering configuration 190 is positioned over the sensor 185, the release liner 112 is removed from the inner surface 194 by pulling on the tab 113, exposing the body-directed surfaces 122 of the electrostatic shield contact pad 120. Next, the outer surface 196 of the overlay covering configuration 190 is pressed to the surface of the skin 184, securing the sensor 185 and overlay covering configuration 190.

Figure 6A:
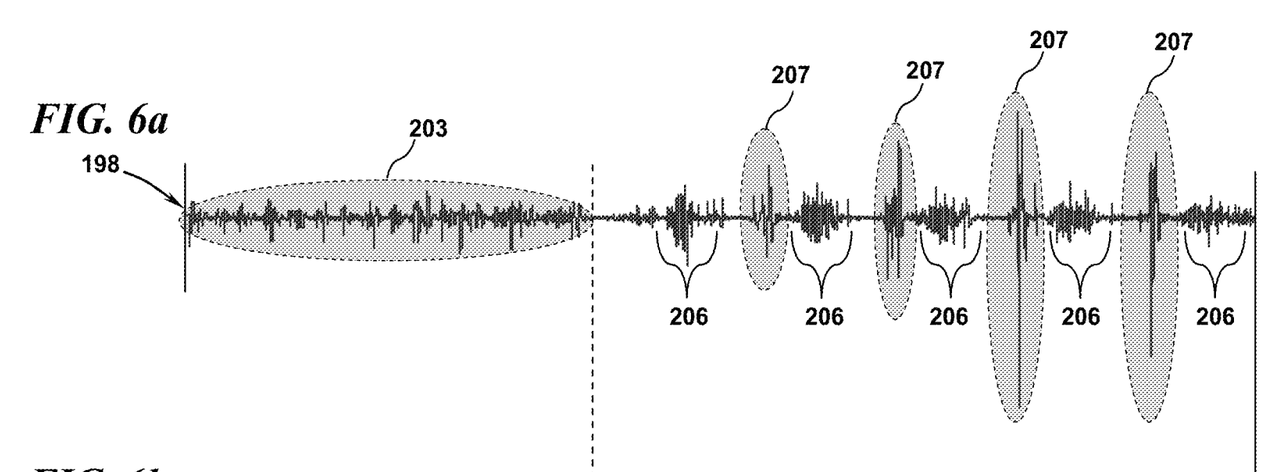
FIG. 6a is a time domain plot of an sEMG sensor signal output when used under clothing during walking, without the presence of an electrostatic shield, showing regions of electrostatic artifact.
Figure 6B:
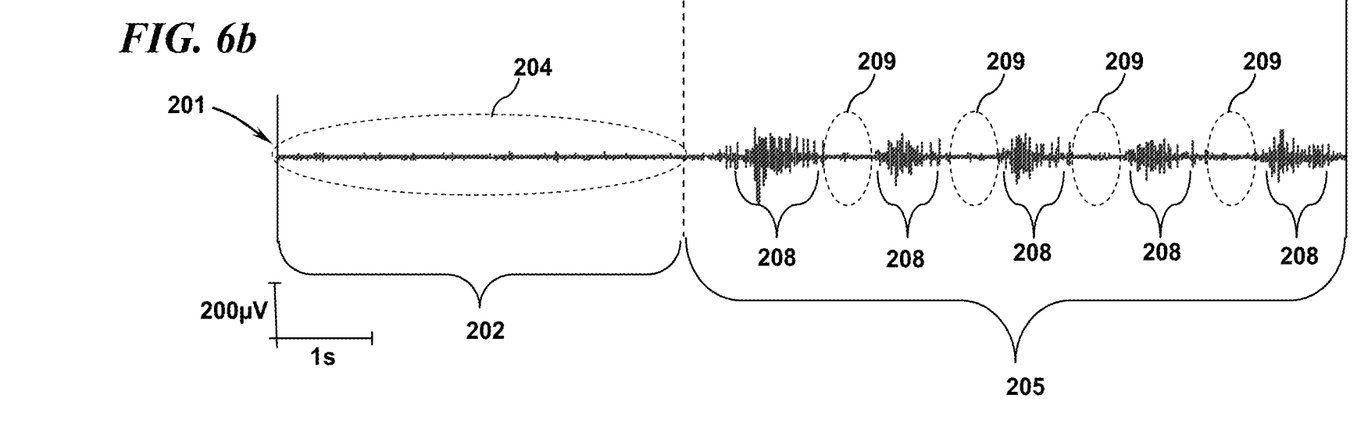
FIG. 6b is a time domain plot of an sEMG sensor signal output when used under clothing during walking, with the incorporation of an electrostatic shield, showing regions where the electrostatic artifact has been suppressed.

FIGS. 6a and 6b are time domain plots of wireless sEMG sensor 185 signal outputs recorded when the sensor was placed under clothing and positioned at location 182 on the upper leg. The signal outputs were recorded during an initial time period of continuous manual rubbing 202 of the clothing against the surface of the sensor while the subject was not contracting their leg muscle, followed by a time period of 5 walking steps 205. FIG. 6a is a signal plot 198 recorded without the presence of an electrostatic shield overlay covering. During the time period of continuous manual rubbing 202, the signal plot 198 exhibits the presence of electrostatically generated artifact signal (encircled shaded region) 203, generated as the result of the triboelectric voltage effect of the clothing rubbing across the sensor's surface. During the time period of walking steps 205, the signal plot 198 exhibits individual bursts of sEMG activity 206 corresponding to a muscle contraction during each step, accompanied by bursts of electrostatically generated signal artifacts (encircled shaded regions) 207 associated with the corresponding periodic clothing contact with the sensor. FIG. 6b is a signal plot 201 recorded with an electrostatic shield overlay covering embodiment 111 placed over the sensor 185. During the time period of continuous manual rubbing 202, the signal plot 201 exhibits the dissipation of the electrostatically generated voltage as show by the absence of artifact signal in the encircled region 204. During the time period of walking steps 205, the signal plot 201 exhibits individual bursts of sEMG activity 208 corresponding to a muscle contraction occurring with each step, accompanied quiescent periods containing no signal artifact (encircled regions) 209, indicating the dissipation of the electrostatically generated voltage corresponding to the periodic clothing contact with the sensor overlay covering 170.

Figure 7A:
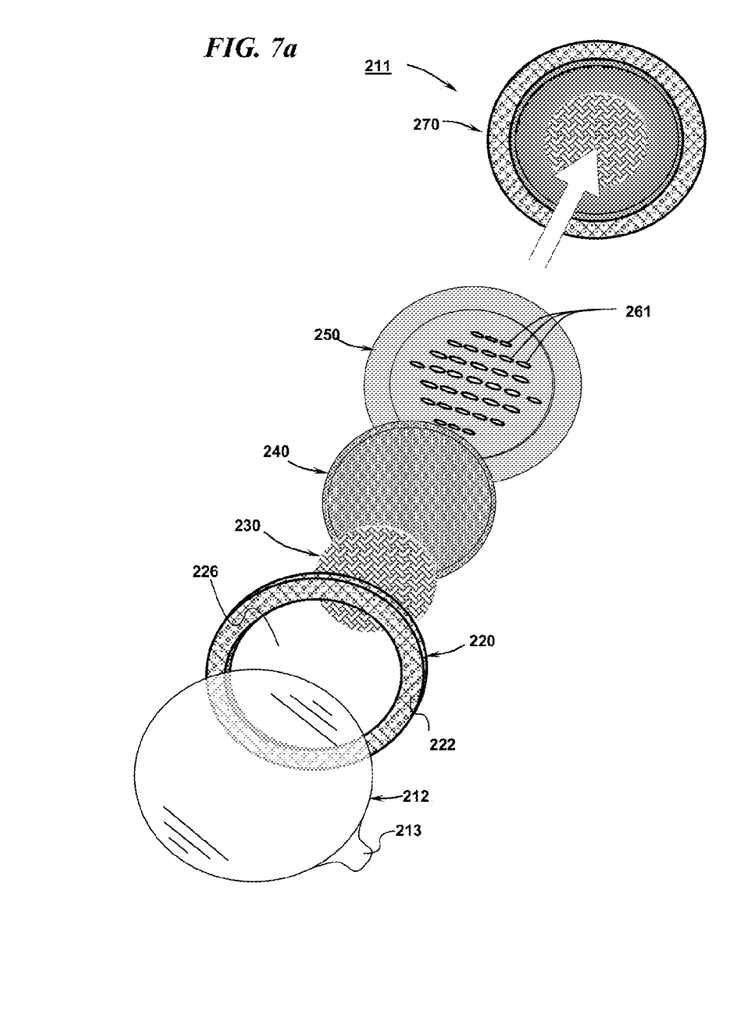
FIG. 7a is an exploded view of a third embodiment of the biomedical sensor overlay covering according to the system described herein.

Another biomedical sensor embodiment 211 includes an electrostatic shield contact pad substrate layer 220, a cushioning substrate layer 230, an insulating substrate layer 240, and an electrostatic shield substrate layer 250, disposed on a release liner 212 as illustrated in the exploded view of FIG. 7a. The assembled components of the sensor overlay covering 211 are in the form of a flexible, patch 270, with a receptacle region shaped and contoured to retain a wireless biomedical sEMG sensor and a conductive adhesive region 272 securing the sensor to the skin. The enclosed geometry of the sensor retaining region 274 of the sensor overlay covering embodiment 211 is in the form of a contoured pocket 277 designed to be compatible with wireless sensor technologies, and provide a means to dissipate the accumulation of electrostatic charges on the covering's outer surface 278 into the body and shield the underlying sensor from externally generated low frequency electrical fields such as power line interference, while maintaining a means of ingress and egress for radio frequency signal reception and transmission for the wireless sensor. The rounded contour of the sensor embodiment 211 enables close placement of adjacent multiple sensors, and provides unencumbered use on smaller muscle groups. The constructional architecture of the sensor overlay covering 211 is similar to sensor embodiment 111 and is detailed in FIG. 7b which shows a top view 280, cross-sectional views 225, 235, 245, 255 of each subsequently added substrate layer, and a cross-sectional view 275 of the assembled components, each of which are individually described.

Figure 7B:
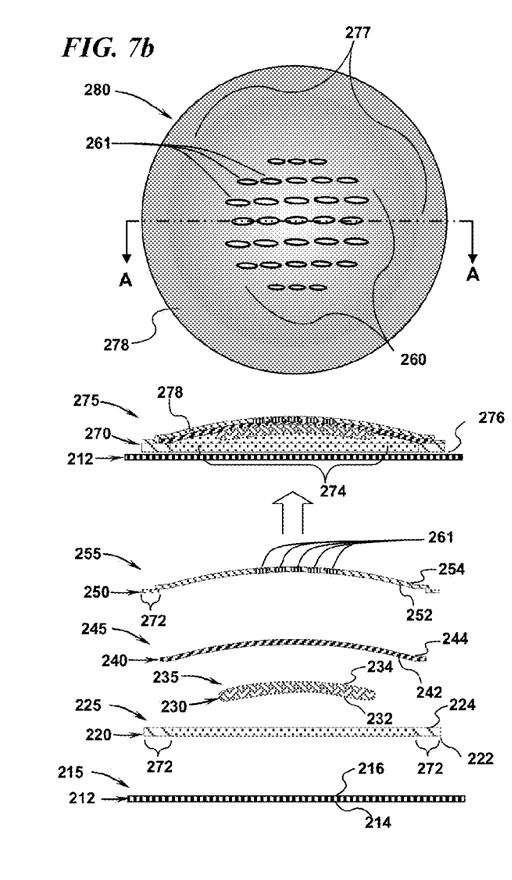

The electrostatic shield contact pad substrate layer 220 of the sensor overlay covering 211 includes a ring shaped sheet of electrically conductive, adhesive, cross-linked hydrophilic polymer gel with a central opening 226, and whose top surface 224 is disposed on region 272 of the bottom surface 252 of the electrostatic shield substrate layer 250 establishing a mechanical and electrical contact with the electrostatic shield substrate layer 250. The electrostatic shield contact pad substrate layer 220 is shaped to match the profile of the region 272 of the electrostatic shield substrate layer 250. The body-directed surface 222 of the electrostatic shield contact pad substrate layer 220 establishes a mechanical and electrical contact between the electrostatic shield substrate layer 250 and the surface of the skin, thereby dissipating electrostatic charges to the body and securing the sensor overlay covering 211.

The cushioning substrate layer 230 of the sensor overlay covering 211 includes a flexible, compliant, mat whose upper surface 234 is disposed on and adhered to the lower surface 242 of the insulating substrate layer 240 so that it makes mechanical contact in retaining region 274. The thickness, compliance and contour of the cushioning substrate layer 230 is selected so that when the sensor overlay covering 211 is applied over a sensor, its lower surface 232 conforms to the upper surfaces of a sensor, thereby retaining and cushioning the sensor from externally applied mechanical disturbances. The cushioning substrate layer 230 component of the sensor overlay covering 211 is formed from a sheet of non-triboelectric, absorbent material with permeability and thickness selected so that it wicks away and retains excessive skin moisture.

The insulating substrate layer 240 of the sensor overlay covering 211 includes a flexible, compliant sheet of electrically insulating material whose upper surface 244 is disposed on and adhered to the lower surface 252 of the electrostatic shield substrate layer 250 so that it makes mechanical contact and forms an electrically insulating barrier between the electrostatic shield 250 and a sensor. The profile of insulating substrate layer 240 is shaped so as to selectively expose the electrically conductive region 272 of the bottom surface 252 of the electrostatic shield substrate layer 250 to the upper surface 224 of the electrostatic shield contact pad substrate layer 220, so as to form an electrical inter-connection between the electrostatic shield layer 250 and contact pad substrate layer 220. The insulating substrate layer 240 is formed from a double-sided adhesive coated sheet of non-triboelectric, material with thickness selected so that it resists electrical breakdown from static electrical discharges (ESD) to the skin.

Figure 8A:
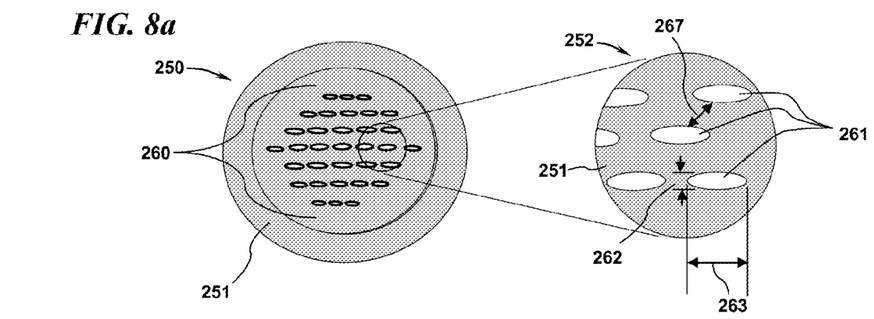
FIG. 8a is an expanded detail view of the electrostatic shield substrate layer of the sensor overlay covering shown in FIG. 7a, showing a conductive substrate with an arrangement of apertures.

The electrostatic shield substrate layer 250 of the sensor overlay covering 211 includes a flexible, compliant layer with electrically conductive properties configured so as to dissipate the accumulation of electrostatic charges on the covering's outer surface 278 into the body and shield the underlying sensor from externally generated low frequency electrical fields such as power line interference, while maintaining a means of ingress and egress for radio frequency signal reception and transmission for the wireless sensor. The contoured region 274 of the electrostatic shield substrate layer 250 is shaped to retain and encase a biomedical sensor. The upper surface 254 of the electrostatic shield substrate layer 250 forms the outer covering 278 of the sensor overlay 211 which is cosmetically textured and colored so that it more closely matches the color and texture of the underlying skin. The exposed region 272 of the body directed surface 252 of the electrostatic shield substrate layer 250 forms a mechanical and electrical inter-connection with the upper surface 224 of the electrostatic shield contact pad substrate layer 220. The contoured pocket region 277 of electrostatic shield substrate layer 250 contains an aperture region 260 formed from a plurality of apertures 261. FIG. 8a is pictorial view of an electrically conductive 251 electrostatic shield substrate layer 250, accompanied by an encircled magnified view 252 showing the plurality of apertures 261 forming the aperture region 260. The height 262, width 263, separation 267, and number of apertures within the aperture region 260 of the electrically conductive 251 electrostatic shield substrate layer 250 are selected to maximize the level of ingress and egress of radio frequency signal reception and transmission for a given radio frequency bandwidth of a wireless sensor while maintaining dissipation of electrostatic fields.

Figure 8B:
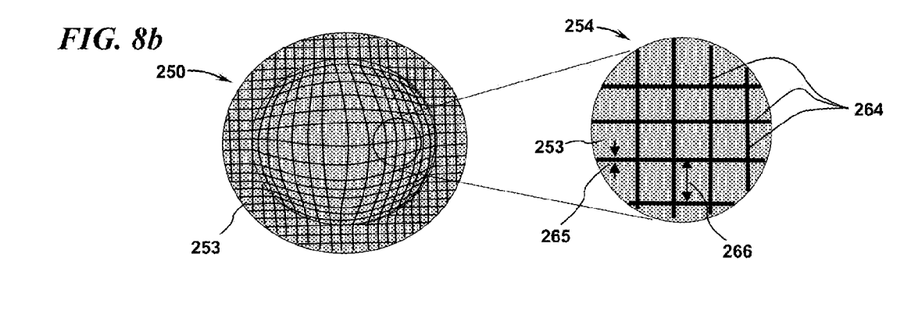
FIG. 8b is an expanded detail view of the electrostatic shield substrate layer of the sensor overlay covering shown in FIG. 7a, showing an non-conductive substrate with an arrangement of conductive traces.
Figure 8C:
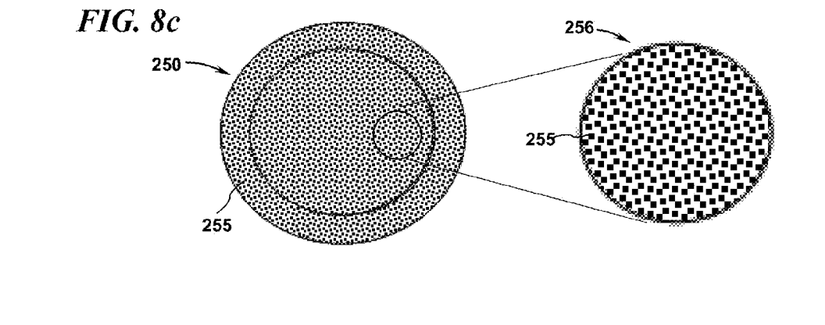
FIG. 8c is an expanded detail view of the electrostatic shield substrate layer of the sensor overlay covering shown in FIG. 7a, showing an electrically resistive substrate.

FIGS. 8b and 8c show two alternative constructional configurations of the of electrostatic shield substrate layer 250. FIG. 8b is pictorial view of an electrically non-conductive 253 electrostatic shield substrate layer 250, accompanied by an encircled magnified view 254 showing the plurality of electrically conductive traces 264 retained in a non-conductive substrate 253. The pattern of traces 264 can be formed using printed circuit board technology, can be formed from a plurality of wires embedded within the electrically non-conductive substrate 253, or formed using other selective conductive trace 264 deposition techniques. The width 265, spacing 266, and number electrically conductive traces 264 are selected to maximize the level of ingress and egress of radio frequency signal reception and transmission for a given radio frequency bandwidth of a wireless sensor while maintaining dissipation of electrostatic fields. FIG. 8c is pictorial view of an electrically resistive 255 electrostatic shield substrate layer 250, accompanied by an encircled magnified view 256 showing the distribution of resistive composition throughout the electrostatic shield substrate layer 250. The bulk resistivity of the substrate 255 is selected to maximize the level of ingress and egress of radio frequency signal reception and transmission for a given radio frequency bandwidth of a wireless sensor while maintaining dissipation of electrostatic fields.

Figures 9A, 9B:
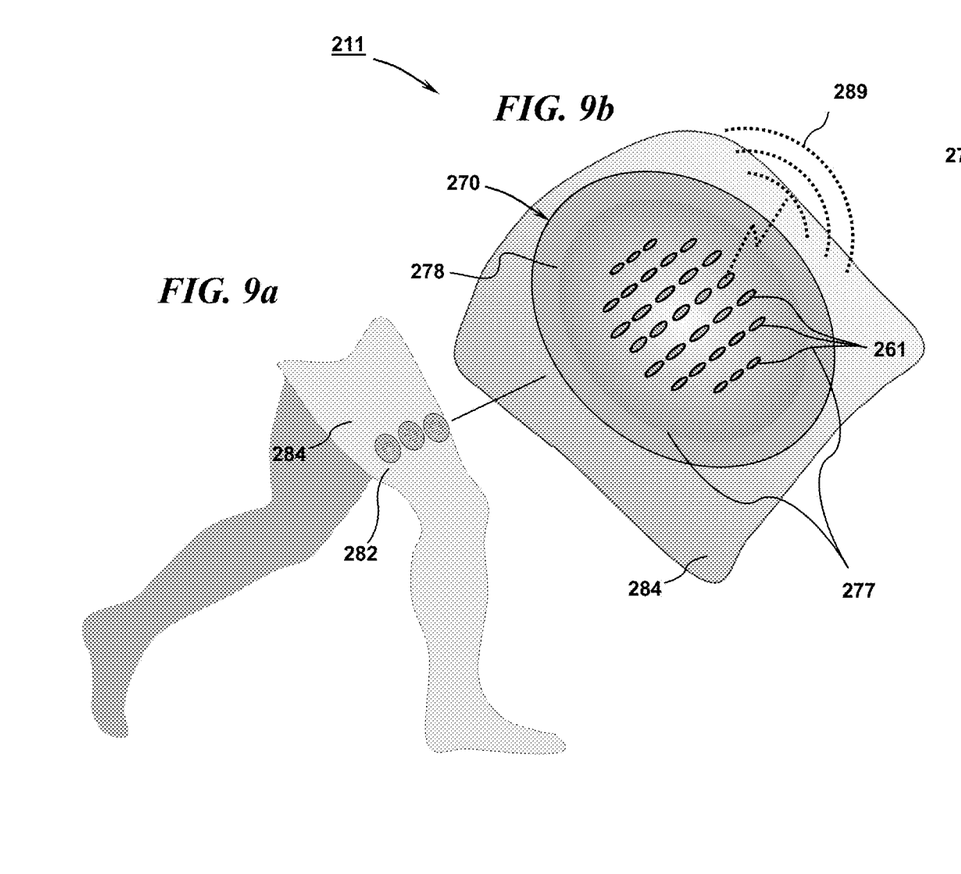
Figure 9C:
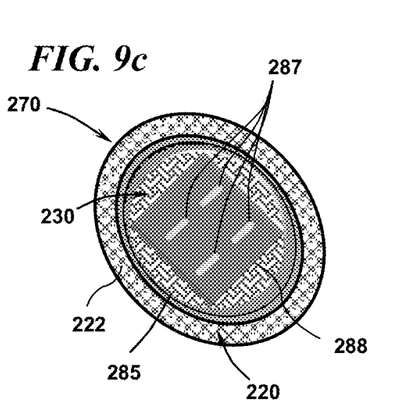
FIG. 9c is a bottom view of the sensor overlay covering shown in FIG. 9b showing the body-directed substrate layers.

Pictorial views of the assembled components of the patch configuration 270 of the sensor overlay covering embodiment 211 are shown in FIGS. 9a, 9b, and 9c. As illustrated in the example use-case in FIG. 9a, the patch overlay configuration 270 is placed on the muscles of the upper leg 282. The example shows a closely spaced array of the patch configuration 270, each retaining a wireless sensor 285 configured for monitoring adjacent muscle groups. FIG. 9b details a close up view of an individual patch overlay configuration 270 positioned on the skin 284. A wireless sensor 285 is retained in a contoured pocket region 277 of overlay configuration 270. FIG. 9c shows a bottom view of the sensor retained in the overlay configuration 270 and arranged so that the sensor's bottom surface 288 containing the sensor contacts 287 and the surface 222 of the electrostatic shield contact pad substrate layer 220 are directed towards the skin. The arrangement of apertures 261 in the sensor overlay covering embodiment 211 provides for the ingress and egress for a radio frequency signal 289.

The patch configuration 270 of the sensor overlay covering embodiment 211 is suitable for securing the sensor at locations which are not amenable to an encircling band, such as the torso and large limb muscles, or for applications where multiple, closely spaced, adjacent sensors are required. The skin 284 application of the patch configuration 270, of sensor overlay covering 211 used the example illustrated in FIG. 5a, is detailed as follows: Initially, the body-directed surface 288 of the sensor 285 containing the electrode contacts 287 is applied to the surface of the skin 284. Prior to use, the release liner 212 of overlay configuration 270 is removed and the retaining region 274 of overlay covering 270 is positioned and pressed into place over the sensor 285. Next, the outer surface 278 of the overlay 270 is pressed to the skin 284, securing the sensor 285 and overlay covering configuration 270.

Obviously, many modifications and variations of the present invention are possible in light of the above teachings. It is to be understood, therefore, that the invention can be practiced otherwise than as specifically described.

What is claimed is:

1. A biomedical sensor overlay covering, comprising:
an electrically conductive contact pad substrate layer having a body-directed surface with an adhesive that adheres to skin of a subject;
an electrically insulating substrate layer having a first surface that is coupled to a surface of the contact pad substrate layer that is opposite to the body-directed surface;
a cushioning substrate layer coupled to the first surface of the electrically insulating substrate layer; and
an electrostatic shield substrate layer coupled to a second surface of the electrically insulating substrate layer that is opposite to the first surface of the electrically insulating substrate layer, the electrostatic shield substrate layer having a retaining region that is shaped to retain and encase a biomedical sensor, wherein the electrostatic shield substrate layer shields the biomedical sensor from external electrical fields and, through an electrical contact with the skin of the subject established with the electrically conductive contact pad, dissipates accumulation of electrostatic charge into a body of the subject, and wherein the cushioning layer makes mechanical contact with the electrically insulating substrate layer at an area corresponding to the retaining region to suppress movement artifact.

2. A biomedical sensor overlay covering as in claim 1, wherein the electrostatic shield substrate layer is an elongated strip with conductive adhesive regions securing the biomedical sensor to the skin.

3. A biomedical sensor overlay covering as in claim 1, wherein the electrostatic shield substrate layer is a continuous band to encircle a limb with conductive adhesive regions securing the biomedical sensor to the skin.

4. A biomedical sensor overlay covering as in claim 3, wherein at least some of the substrate layers contain segments of stretchable elastic providing compliance with underlying skin tissue.

5. A biomedical sensor overlay covering as in claim 1, wherein the substrate layers form a patch with conductive adhesive regions securing the biomedical sensor to the skin.

6. A biomedical sensor overlay covering as in claim 1, wherein the electrostatic shield substrate layer is formed from an electrically conductive metallic sheet.

7. A biomedical sensor overlay covering as in claim 6, wherein the electrostatic shield substrate layer is formed with a plurality of apertures.

8. A biomedical sensor overlay covering as in claim 1, wherein the electrostatic shield substrate layer is formed from an electrically conductive plastic sheet.

9. A biomedical sensor overlay covering as in claim 8, wherein the electrostatic shield substrate layer is formed with a plurality of apertures.

10. A biomedical sensor overlay covering as in claim 1, wherein the electrostatic shield substrate layer is formed from electrically resistive material.

11. A biomedical sensor overlay covering as in claim 10, wherein the electrostatic shield substrate layer is formed with a plurality of apertures.

12. A biomedical sensor overlay covering as in claim 10, wherein the electrostatic shield substrate layer provides ingress and egress for radio frequency signal reception and transmission.

13. A biomedical sensor overlay covering as in claim 1, wherein the electrostatic shield substrate layer is formed from electrically non-conductive material with a plurality of electrically conductive traces.

14. A biomedical sensor overlay covering as in claim 13, wherein the electrically conductive traces for the electrostatic shield substrate layer are formed from electrically conductive printed circuit traces.

15. A biomedical sensor overlay covering as in claim 13, wherein the electrostatic shield substrate layer provides ingress and egress for radio frequency signal reception and transmission.

16. A biomedical sensor overlay covering as in claim 1, wherein the electrostatic shield substrate layer is formed from electrically resistive material with a plurality of electrically conductive traces.

17. A biomedical sensor overlay covering as in claim 16, wherein the electrically conductive traces for the electrostatic shield substrate layer are formed from electrically conductive printed circuit traces.

18. A biomedical sensor overlay covering as in claim 1, wherein the electrically conductive contact pad substrate layer is formed from electrically conductive, adhesive, cross-linked hydrophilic polymer gel establishing a mechanical and electrical contact with a surface of the skin.

19. A biomedical sensor overlay covering as in claim 18, wherein the electrically conductive contact pad substrate layer is contoured to match a profile of the electrostatic shield substrate layer, and is adhered to a lower surface of the electrostatic shield substrate layer to make mechanical and electrical contact with selectively exposed electrically conductive regions of the electrostatic shield substrate layer, thereby dissipating electrostatic charges to the body through contact with a skin surface of the body.

20. A biomedical sensor overlay covering as in claim 1, wherein the electrically insulating substrate layer is contoured to match a profile of the electrostatic shield substrate layer and shaped so as to selectively expose electrically conductive regions of the electrostatic shield substrate layer, and is adhered to a lower surface of the electrostatic shield substrate layer to make mechanical contact.

21. A biomedical sensor overlay covering as in claim 20, wherein the electrically insulating substrate layer is formed from an insulating membrane with a double-sided adhesive coating.

22. A biomedical sensor overlay covering as in claim 1, wherein the cushioning substrate layer is contoured and shaped to match upper surfaces of the biomedical sensor and is adhered to a lower surface of the electrical insulating substrate layer to make mechanical contact.

23. A biomedical sensor overlay covering as in claim 22, wherein the cushioning substrate layer is formed from an absorbent material arranged to wick away and retain excessive skin moisture.

24. A biomedical sensor overlay covering as in claim 1, wherein the overlay covering is formed from materials that are hypoallergenic, breathable, and designed for use without slippage or skin breakdown.

25. A biomedical sensor overlay covering as in claim 1, wherein the overlay covering is cosmetically textured and colored to more closely match color and texture of underlying skin.

26. A biomedical sensor overlay covering as in claim 1, wherein body-directed adhesive surfaces of the overlay covering are mounted on a release liner.

27. A biomedical sensor as in claim 1, wherein the sensor is single use and disposable.

* * * * *